(12) United States Patent
Hsu

(10) Patent No.: US 7,029,136 B2
(45) Date of Patent: Apr. 18, 2006

(54) LIGHT SHIELD FOR WELDING

(76) Inventor: Ming Kun Hsu, 235 Chung-Ho P.O. Box 8-24, Taipei (TW)

( * ) Notice: Subject to any disclaimer, the term of this patent is extended or adjusted under 35 U.S.C. 154(b) by 118 days.

(21) Appl. No.: 10/853,366

(22) Filed: May 26, 2004

(65) Prior Publication Data

US 2005/0264892 A1    Dec. 1, 2005

(51) Int. Cl.
*A61F 9/06*    (2006.01)
(52) U.S. Cl. .................. 359/601; 2/8; 2/11; 219/147
(58) Field of Classification Search .......... 359/599, 359/601–614; 2/8, 11; 219/147
See application file for complete search history.

(56) References Cited

U.S. PATENT DOCUMENTS

| 1,664,804 | A | * | 4/1928 | Allen ............................. 2/11 |
| 1,759,317 | A | * | 5/1930 | Malcom ......................... 2/11 |
| 2,045,802 | A | * | 6/1936 | Walther ................. 340/815.73 |
| 2,210,370 | A | * | 8/1940 | Herradora ................. 219/147 |
| 2,962,721 | A | * | 12/1960 | Espy ............................... 2/11 |
| 3,908,197 | A | * | 9/1975 | Griffin ............................ 2/20 |
| 4,161,643 | A | * | 7/1979 | Martin et al. ................ 219/70 |
| 4,332,004 | A | * | 5/1982 | Slaughter .................... 362/105 |
| 5,241,154 | A | * | 8/1993 | Estrate ....................... 219/147 |

FOREIGN PATENT DOCUMENTS

DE    29911660 U1 *    9/1999

\* cited by examiner

*Primary Examiner*—Drew A. Dunn
*Assistant Examiner*—Mark Consilvio

(57) ABSTRACT

A light shield for eye protection in the welding process comprises a holding unit, a base plate, a filter plate and a universal joint. The filter plate, in conjunction with the base plate, is mounted on a universal joint by which the tilt angle thereof with respect to the holding unit can be free adjusted. Since the filter plate is applied closely to the welding target, the area thereof is small, significantly reducing the weight of the light shield. The base plate further includes a lamp for illuminating the welding target, so that welding can be conveniently done in dark places. The holding unit is for retaining a hand of a user, leaving the fingers of the hand for handling other parts.

5 Claims, 4 Drawing Sheets

LIGHT SHIELD FOR WELDING

FIELD OF THE INVENTION

The present invention relates to light shields for welding, and more particularly to a light shield for welding having the advantages as follows.
(1) The light shield for welding comprises a holding unit, a universal joint, a base plate and a filter plate. The holding unit can be attached to a palm so that retaining the shield by fingers is not necessary, and therefore the fingers can hold other things. The area of the filter plate is smaller than those of the conventional light shields, whereas the light shielding effect is the same, so that the light shield is more compact and lighter. It is a further advantage that the filter plate can be adjusted to a wide range of tilt angles using the universal joint.
(2) The base plate further includes a power supply unit and a lamp for providing illumination for welding in dark places.
(3) The base plate and the filter plate can be replaced when they are damaged or worn out.

BACKGROUND OF THE INVENTION

Welding is a method using electrically melted metallic materials to joint different metallic parts, during which very bright light is produced. The light can bring hazardous effects to a user's eyes and skin, and hence light shield for personnel protection is necessary.

Referring to FIG. 1, a light shield for welding of the prior art comprises a block board 1 having a large area, a light filter plate 2 embedded within the block board 1 for viewing the target being welded, and a handle 3 for holding the light shield by a hand.

The light shield for welding of the prior art has the disadvantages as follows.
(1) Since two hands are necessary respectively for holding the handle 3 and a welding tool during the welding process, there is no a further hand to retain the parts being welded.
(2) The size of the light shield is large and heavy and therefore inconvenient to a user.
(3) To provide a better eye protection, the filter plate 2 is optically dense, and a user has to shift his or her head close to the block board 1 so as to view the target clearly. Therefore, the filter plate 2 and the block board 1 have to be large enough to protect the user, making the light shield significantly heavier than the present invention.
(4) The light shield for welding of the prior art usually does not have a lamp for illuminating the target being welded, and therefore working in dark places is not convenient.

SUMMARY OF THE INVENTION

Accordingly, the primary objective of the present invention is to provide a light shield for welding comprising a holding unit, a universal joint, a base plate and a filter plate. The holding unit can be attached to a palm so that retaining the shield by fingers is not necessary, and therefore the fingers can hold other things. The area of the filter plate is smaller than those of the conventional light shields, whereas the light shielding effect is the same, so that the light shield is more compact and lighter. It is a further advantage that the filter plate can be adjusted to a wide range of tilt angles using the universal joint.

The secondary objective of the present invention is to provide a light shield for welding wherein the base plate further includes a power supply unit and a lamp for providing illumination for welding in dark places, so that a welding job can be accurately done.

It is a further objective of the present invention that the base plate and the filter plate can be replaced when they are damaged or worn out.

The various objects and advantages of the present invention will be more readily understood from the following detailed description when read in conjunction with the appended drawings.

DETAILED DESCRIPTION OF THE PREFERRED EMBODIMENTS

Figure 1:
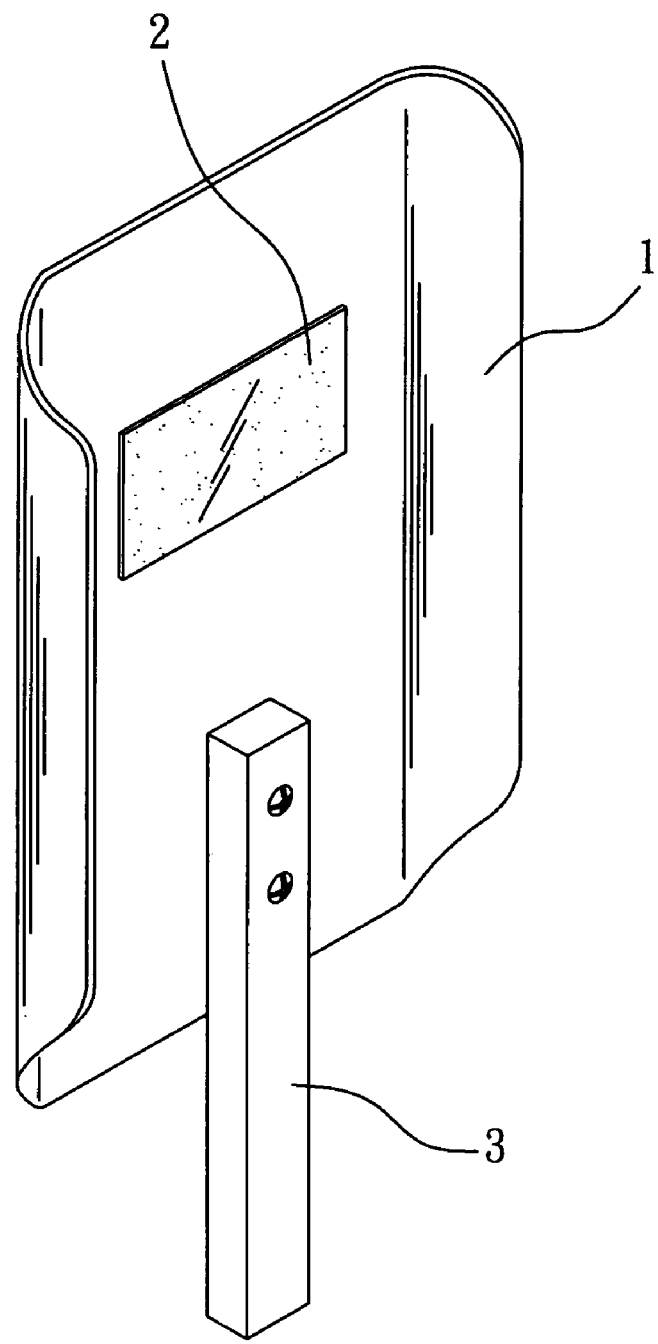
FIG. 1 is a perspective view of a light shield for welding of the prior art.
Figure 2:
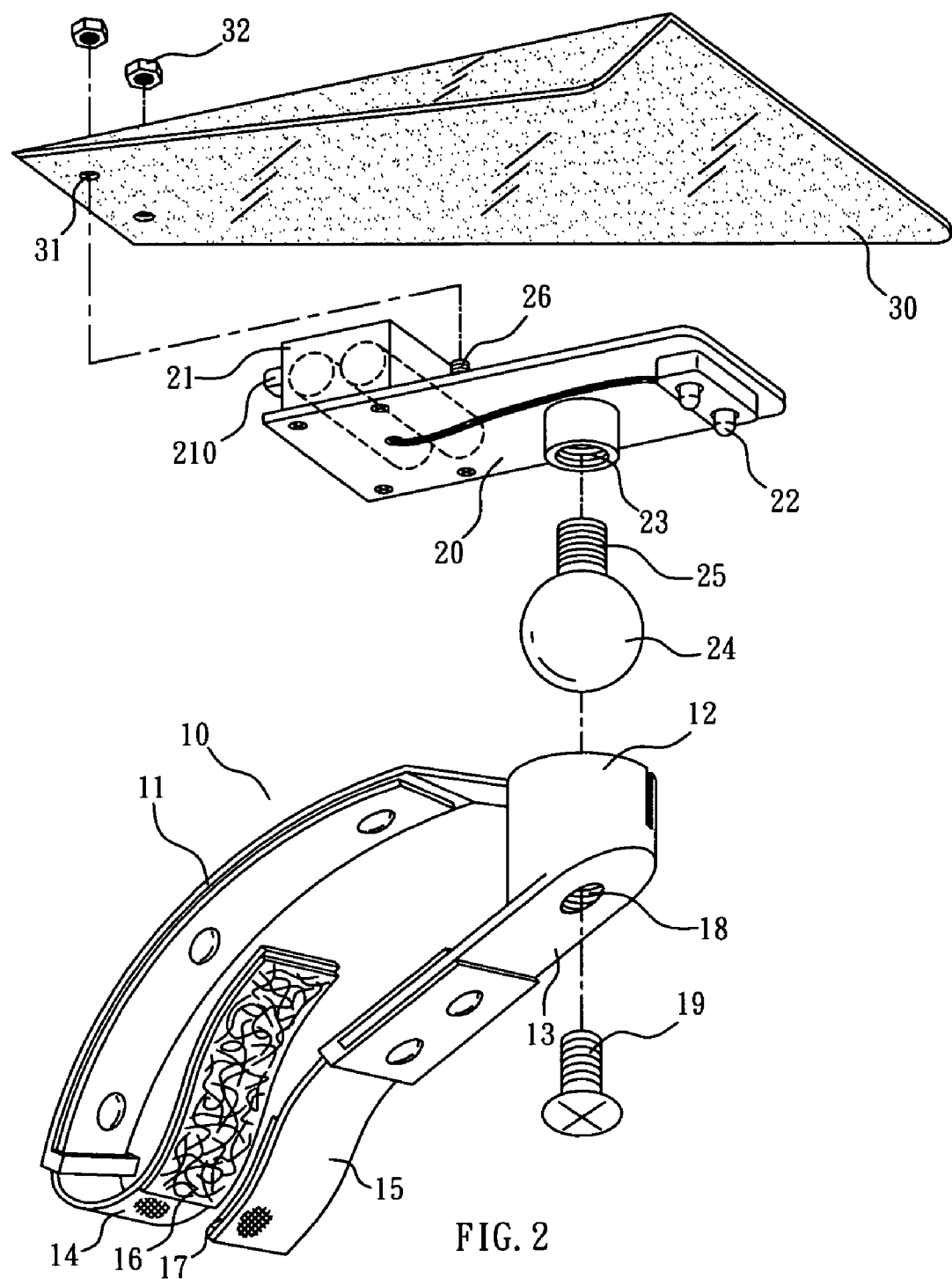
FIG. 2 is an exploded perspective view of a light shield for welding according to the present invention.
Figure 3:
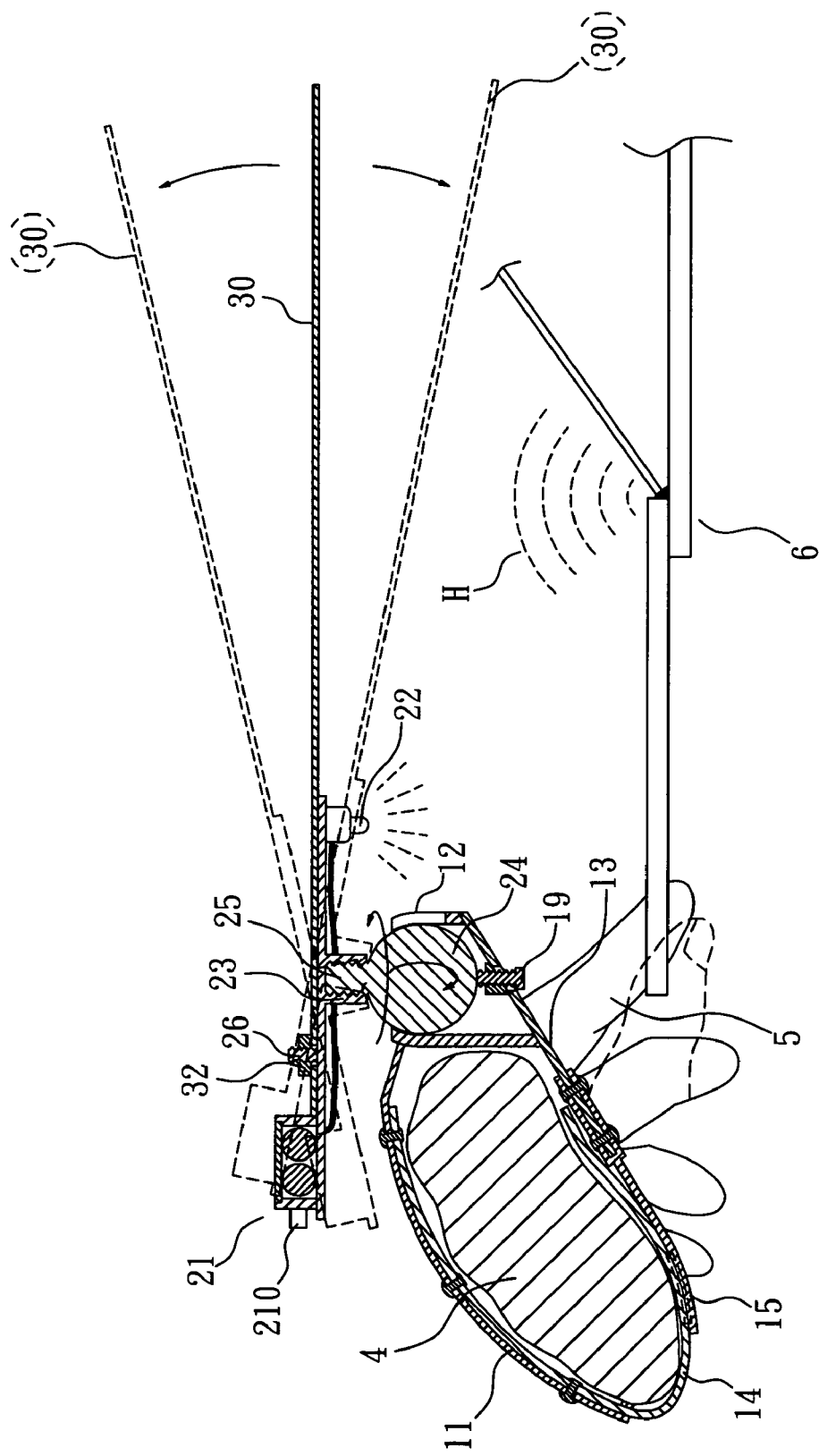
FIG. 3 is a cross-sectional view of a light shield for welding according to the present invention, illustrating the adjustment of the vertical angle of the filter plate.
Figure 4:
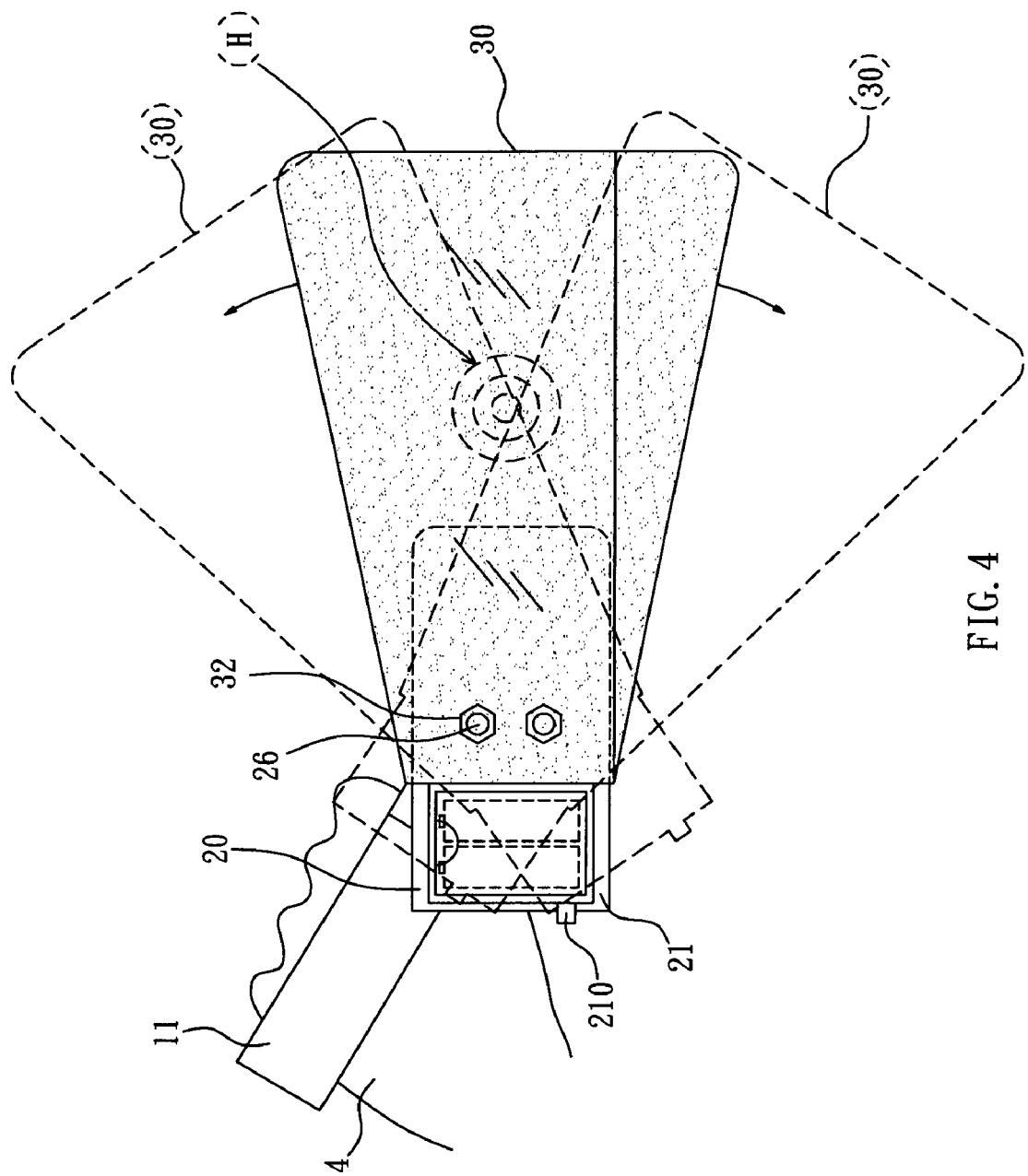
FIG. 4 is a top view of a light shield for welding according to the present invention, illustrating the adjustment of the horizontal angle of the filter plate.

Referring to FIGS. 2, 3 and 4, a light shield for welding according to the present invention comprises a holding unit 10, a universal joint 24, a base plate 20 and a filter plate 30.

The holding unit 10 further includes an upper holding plate 11, a connecting barrel 18 and a lower holding plate 13. The upper holding plate 11 and the lower holding plate 13 are integrally extended from the connecting barrel 12, the free ends of which are respectively provided with straps 14, 15 and touch fasteners 16, 17. Thereby, a palm 4 can be retained between the upper holding plate 11 and the lower holding plate 13, and the light shield is held without using fingers.

The universal joint 24 is substantially a spherical body situating within the connecting barrel 12 of the holding unit 10. The caliber of the opening of the connecting barrel 12 is tapered inward so that the universal joint 24 is rotationally secured therein, having a rod portion extended out of the connecting barrel 12. Further, the connecting barrel 12 of the holding unit 10 can be provided with a screw hole 18 for receiving a retaining screw 19; the retaining screw 19 is for restricting the rotational motion of the universal joint 24 within the connecting barrel 12.

The base plate 20 is connected to the universal joint 24 on the lower side thereof and to the filter plate 30 on the upper side thereof. The base plate 20 further includes a power supply unit 21 having a switch 210 and at least one battery. The lower side of the base plate 20 is provided with a lamp 22 for illuminating the target being welded. The connecting mechanism of the universal joint 24 and the base plate 20 comprises a screw base 24 for retaining a screw rod 25 extended from the universal joint 24. The connecting mechanism of the base plate 20 and the filter plate 30 comprises a plurality of through holes 31 on the filter plate 30 and a corresponding plurality of screw pins 26 on the base plate 20, thereby the screw pins 26 being inserted into the through holes 31 and secured by a plurality of screw nuts 32.

As shown in FIGS. 3 and 4, to use the light shield for welding, a palm 4 is inserted into the holding unit 10, and the straps 14, 15 and the tough fasteners 16, 17 then fasten the upper holding plate 11 and the lower holding plate 13. The filter plate 30 is then closely applied to a welding part 6 for filtering the optical radiation H produced during the welding process.

The light shield for welding aforesaid has the advantages as follows.

(1) Instead of being applied to eyes, the filter plate 30 is brought close to the welding part 6. Since welding substantially occurs at a point in space, a filter plate 30 of small area is sufficient to provided the desired light shielding.

(2) Instead of being applied to eyes, the filter plate 30 is brought close to the welding part 6. The welding part 6 underneath the filter plate 30 can be clearly seen. Further, the face of a user needs not to approach to light shield, and the welding job becomes more comfortable.

(3) The holding unit 10 is attached to the palm 4, without using the fingers 5. Therefore, the fingers can be used to handle the welding part 6.

(4) The welding part 6 is illuminated by the lamp 22 powered by the power supply unit 21, which can bright up the welding part 6 blurred by the filter plate 30.

(5) The universal joint 24 connecting the holding unit 10 with the base plate 20 and the filter plate 30. Both the vertical and the horizontal title angles of the filter plate 30 with respect to the holding unit 10 can be freely adjusted, as shown in FIGS. 3 and 4.

(6) A retaining screw 9 is used to restrict the motion of the universal joint 24 once its angular position is set.

(7) The filter plate 30 is attached to the base plate 20 by screw pins 26 and thereby replaceable.

(8) Since the area of the filter plate 30 is small and the light shield is attached to the palm 4, the light shield can be used in other occasions rather than welding, such as grinding and cutting, for preventing ejection of small debris hurting the user.

(9) The lamp 22 powered by the power supply unit 21 allows the present invention to be used as a flashlight.

The present invention is thus described, and it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A light shield for welding, comprising:

a holding unit having an upper holding plate and a lower holding plate each extended from a connecting barrel, said upper holding plate and said lower holding plate each having a strap and a touch fastener for fastening a palm therein;

a universal joint being substantially a spherical body and rotatably secured within said connecting barrel, said universal joint being capable of rotating freely in said connecting barrel;

a base plate connected to said universal joint on a lower side thereof and to said filter plate on an upper side thereof; and a filter plate made of an optically opaque material for blocking lights produced in a welding process;

whereby said light shield for welding can be attached to a hand without using the fingers of said hand, and whereby said filter plate can be adjusted about said universal joint to have a wide range of vertical and horizontal tilt angles with respect to said holding unit.

2. The light shield for welding of claim 1 wherein said connecting barrel of said holding unit further comprises a screw hole and a retaining screw for restricting said universal joint in said connecting barrel and therefore for fixing said tilt angles of said filter plate.

3. The light shield for welding of claim 1 wherein said universal joint further includes a screw rod, and said base plate further includes a screw base; said screw rod is secured in said screw base, thereby connecting said universal joint with said base plate.

4. The light shield for welding of claim 1 wherein said base plate further includes a plurality of screw pins, and said filter plate further includes a plurality of corresponding through holes, thereby said screw pins going through said through holes and further being secured by a plurality of screw nuts, and whereby said filter plate is replaceable.

5. The light shield for welding of claim 1 wherein said base plate further includes a lamp and a power supply unit having at least one battery and a switch for illuminating an object being welded.

* * * * *